United States Patent
Bae et al.

(10) Patent No.: US 8,557,590 B2
(45) Date of Patent: Oct. 15, 2013

(54) METHOD FOR MEASURING GLYCATED HEMOGLOBIN

(75) Inventors: Byeong-Woo Bae, Anyang-si (KR); Sung-Dong Lee, Anyang-si (KR); Hyong-Soo Kim, Suwon-si (KR)

(73) Assignee: Infopia Co., Ltd., Anyang-si (KR)

( * ) Notice: Subject to any disclaimer, the term of this patent is extended or adjusted under 35 U.S.C. 154(b) by 22 days.

(21) Appl. No.: 13/329,689

(22) Filed: Dec. 19, 2011

(65) Prior Publication Data

US 2012/0088253 A1 Apr. 12, 2012

Related U.S. Application Data

(63) Continuation of application No. PCT/KR2009/003303, filed on Jun. 19, 2009.

(51) Int. Cl.
*G01N 33/72* (2006.01)
*C12M 1/34* (2006.01)
*G01N 33/543* (2006.01)
*G01N 1/18* (2006.01)

(52) U.S. Cl.
USPC ............ 436/67; 436/518; 436/522; 436/523; 436/527; 436/541; 436/66; 436/175; 436/177; 436/178; 435/7.1; 435/7.25; 435/287.2; 435/287.7

(58) Field of Classification Search
USPC ................ 435/7.1, 7.25, 287.1, 287.2, 287.7, 435/287.9; 436/518, 522, 523, 527, 528, 436/533, 538, 541, 17, 66, 67, 175, 177, 436/178
See application file for complete search history.

(56) References Cited

U.S. PATENT DOCUMENTS

| 5,242,842 | A | 9/1993 | Sundrehagen |
| 6,300,142 | B1 | 10/2001 | Andrewes et al. |
| 6,316,265 | B1 | 11/2001 | Lee et al. |
| 6,339,293 | B1 | 1/2002 | Kimiya et al. |
| 6,562,581 | B2 | 5/2003 | Law et al. |
| 7,186,566 | B2 * | 3/2007 | Qian .............................. 436/524 |
| 2009/0093012 | A1 * | 4/2009 | Bae et al. ......................... 435/29 |

FOREIGN PATENT DOCUMENTS

| EP | 2 047 909 A2 * | 4/2009 | ............... B01L 3/00 |
| EP | 2047909 A2 | 4/2009 | |
| JP | 3340129 B2 | 11/2002 | |

(Continued)

OTHER PUBLICATIONS

European Search Report issued Oct. 16, 2012 in counterpart European Patent Application No. 09846223.7 (5 pages, in English).

*Primary Examiner* — Gail R Gabel
(74) *Attorney, Agent, or Firm* — NSIP Law (57) ABSTRACT

A method for measuring glycated hemoglobin includes hemolyzing a blood sample with a hemolysate; reacting the hemolyzed blood sample with bead conjugates in which beads are conjugated with glycated hemoglobin binding materials; measuring the amount of total hemoglobin in the reacted blood sample; isolating normal hemoglobin from the glycated hemoglobin conjugated with the bead conjugates; measuring the amount of glycated hemoglobin isolated from the normal hemoglobin; and determining the percentage of the glycated hemoglobin in the blood sample on the basis of the measured amounts of total hemoglobin and glycated hemoglobin. The isolation of normal hemoglobin is performed by absorbing the normal hemoglobin using an absorption pad that is a porous pad having pores, each of which has a size greater than the size of the normal hemoglobin and smaller than the size of the bead.

8 Claims, 5 Drawing Sheets

(56) References Cited

FOREIGN PATENT DOCUMENTS

| KR | 10-2004-0018893 A | 3/2004 |
| KR | 10-2006-0009665 B1 | 2/2006 |
| KR | 10-2007-0014292 B1 | 2/2007 |
| KR | 10-0776394 | 11/2007 |
| KR | 10-0798471 B1 | 1/2008 |
| WO | WO 92/22818 * | 12/1992 ........... G01N 33/543 |
| WO | WO 92/22818 A1 | 12/1992 |

* cited by examiner

: BEAD-BINDING MATERIAL

: HbA1C

METHOD FOR MEASURING GLYCATED HEMOGLOBIN

CROSS REFERENCE TO RELATED APPLICATION(S)

This application is a continuation of International Patent Application No. PCT/KR2009/003303, filed on Jun. 19, 2009, the entire disclosures of which is incorporated herein by reference for all purposes.

TECHNICAL FIELD

The present invention relates to a method for measuring glycated hemoglobin which is used to test for diabetes, and more particularly, to a method for measuring glycated hemoglobin in a further simplified process.

BACKGROUND ART

In the fields of medical diagnosis or drug-based therapy, the concentration measurement of analytes of anesthetics or harmful chemicals has recently been useful in medical or environmental fields. Above all, the concentration measurement of biological samples used in the fields of medical diagnosis and therapy is drawing increasing interest along with an increase in human desire to be free from various diseases. Particularly, with regard to diabetes, a glycated hemoglobin test capable of measuring blood sugar allows a relatively long-term average value of the blood sugar to be obtained by one measurement, and thus is drawing increasing interest.

It has been known that diabetes, which is one cause of adult kidney disease, can reduce the expected value of a mean life span by 15 years. The control of blood sugar to a lower value has been known to be able to prevent chronic complications caused by diabetes.

Hemoglobin $A_{1c}$ (Hb $A_{1c}$) is called glycated hemoglobin, and is present in red blood cells as a part of hemoglobin. When a concentration of blood sugar (glucose) in blood is raised, a glucose moiety is conjugated to hemoglobin. This hemoglobin conjugated with the glucose is referred to as glycated hemoglobin or Hb $A_{1c}$. A value of the glycated hemoglobin is in equilibrium with a value of blood sugar over the last two to three months, and thus the glycated hemoglobin value may be recognized as the blood sugar value for the last two to three months. The glycated hemoglobin value is checked and used as an index for glycosuria management and future drug control. As such, it is important to measure the glycated hemoglobin.

The glycated hemoglobin has a structure in which the glucose is conjugated to the N-terminal valine in the β-chain hemoglobin in the blood, and only a glucose moiety must be specifically detected and measured to distinguish it from the hemoglobin. This moiety is measured in a variety of methods, of which a method using an antibody and borate affinity chromatography are widely used.

To quantitatively measure the glycated hemoglobin value, a fraction of an amount of glycated hemoglobin on the basis of an amount of total hemoglobin is given because the amount of total hemoglobin is different for everyone. Here, the amount of total hemoglobin is measured together. The amount of total hemoglobin generally has a range of 13.0 to 17.0 g/dl for adult men, a range of 12.0 to 15.0 g/dl for adult women, and a range of 11.0 to 14.0 g/dl for infants. When the glycated hemoglobin value is 6.0%, it may be expressed that three-month blood sugar is maintained to 120 g/dl on average.

The American Diabetes Association (ADA) recommends that the glycated hemoglobin value be maintained to 7.0% or less, and a normal range thereof is 4.0 to 6.5%.

Meanwhile, in U.S. Pat. Nos. 5,242,842, 6,339,293, and 6,300,142, a signal generation material such as a dye is additionally required, and thus a measuring step is troublesome. In JP3340129, a diluting step is additionally required. Thus, additional steps must be performed as well. That is, this work requires a measurer to directly intervene in several steps, which may be troublesome to the measurer. Further, the intervention of the measurer may complicate a measuring process, and thus a measuring time is delayed.

Accordingly, there is a need for a method for easily measuring a concentration of the glycated hemoglobin in the whole blood sample by performing a further simplified procedure.

DISCLOSURE

Technical Problem

The present invention is directed to a method of easily measuring a concentration of glycated hemoglobin in a further simplified process than the related art.

Technical Solution

One aspect of the present invention provides a method for measuring glycated hemoglobin, which comprises: a hemolysis step of hemolyzing a blood sample with a hemolysate; a reaction step of reacting the hemolyzed blood sample with bead conjugates in which beads are conjugated with glycated hemoglobin binding materials; a first measuring step of measuring an amount of total hemoglobin in blood; an isolation step of isolating normal hemoglobin from the glycated hemoglobin conjugated with the bead conjugates; a second measuring step of measuring an amount of glycated hemoglobin in blood; and a calculation step of calculating a concentration of the glycated hemoglobin in the blood sample on the basis of the measured amounts of total hemoglobin and glycated hemoglobin in the blood sample.

Here, the hemolysis and reaction steps may be implemented as a single step by putting the hemolysate and the bead conjugates into the blood sample at the same time.

The hemolysate may be selected from the group consisting of TRIS, HEPES, TES, and PIPES.

The bead may be at least one of an agarose bead, a cellulose bead, a sepharose bead, a polystyrene bead, a polymethylmethacrylate bead, a polyvinyltoluene bead, and a glass bead.

The glycated hemoglobin binding material may be at least one of boronic acid, concanavalin A, and an antibody.

The first and second measuring steps may be performed on the basis of light reflection measurement using an optical sensor.

The isolation step may be performed by supplying a washing solution.

The washing solution may be selected from the group consisting of TRIS, HEPES, TES, and PIPES reacting within a range of pH 7 to 8.5.

The isolation step may be performed by absorbing the normal hemoglobin using an absorption pad.

The absorption pad may be a porous pad.

Pores of the porous pad may have a size greater than that of the hemoglobin and smaller than that of the bead.

Advantageous Effects

According to the method for measuring glycated hemoglobin, the amount of total hemoglobin is measured from the whole blood sample including the glycated hemoglobin conjugated with the bead conjugates in which the beads are conjugated with the glycated hemoglobin binding materials and the normal hemoglobin. Thereby, the measuring step is further simplified. Since a separate dye for signal amplification is not required, it is possible to more easily measure the concentration of glycated hemoglobin in the blood sample.

BEST MODE

The present invention is intended to resolve problems of the related art as described above, and an object of the present invention is to provide a method capable of more easily measuring glycated hemoglobin in a blood sample.

In greater detail, according to an aspect of the present invention, there is provided a method for measuring glycated hemoglobin, which comprises: a hemolysis step of hemolyzing a blood sample with a hemolysate; a reaction step of reacting the hemolyzed blood sample with bead conjugates in which beads are conjugated with glycated hemoglobin binding materials; a first measuring step of measuring an amount of total hemoglobin in blood; an isolation step of isolating normal hemoglobin from the glycated hemoglobin conjugated with the bead conjugates; a second measuring step of measuring an amount of glycated hemoglobin in blood; and a calculation step of calculating a concentration of the glycated hemoglobin in the blood sample on the basis of the measured amounts of total hemoglobin and glycated hemoglobin in the blood sample Hereinafter, the present invention will be described in detail.

The concentration of glycated hemoglobin in the blood sample is measured relative to the amount of total hemoglobin in the blood. As such, to measure the concentration of the glycated hemoglobin, the hemolysis step of hemolyzing the blood sample to expose the normal hemoglobin and the glycated hemoglobin contained in the blood is performed.

Here, the hemolysate that can be used has a buffer concentration of osmotic pressure under which hemolysis is possible and pH of 7 to 8.5, and is preferably selected from a group consisting of TRIS, HEPES, TES, and PIPES. More preferably, the hemolysate is a buffer solution containing a surfactant, for instance 20 mM HEPES buffer solution (N-2-Hydroxyethylpiperazine-N'-2-ethanesulfonic acid HEPES; pH 8.1). However, the hemolysate is not limited to these solutions, and any adequate solutions that have been widely known in the related art may be used. The hemoglobin and the glycated hemoglobin coexist in the hemolyzed blood sample.

Then, the reaction step of reacting the hemolyzed blood sample with the bead conjugates in which the beads are conjugated with the glycated hemoglobin binding materials is performed. The term "bead conjugate" used herein means that the beads are conjugated to binding materials that can be conjugated to the glycated hemoglobin. The bead conjugates are attached to the glycated hemoglobin by the glycated hemoglobin binding materials. The term "glycated hemoglobin binding material" used herein refers to a material that can be specifically conjugated to the glycated hemoglobin. For instance, at least one of boronic acid, concanavalin A, and an antibody, and preferably boronic acid, may be used as the glycated hemoglobin binding material.

Figure 1:
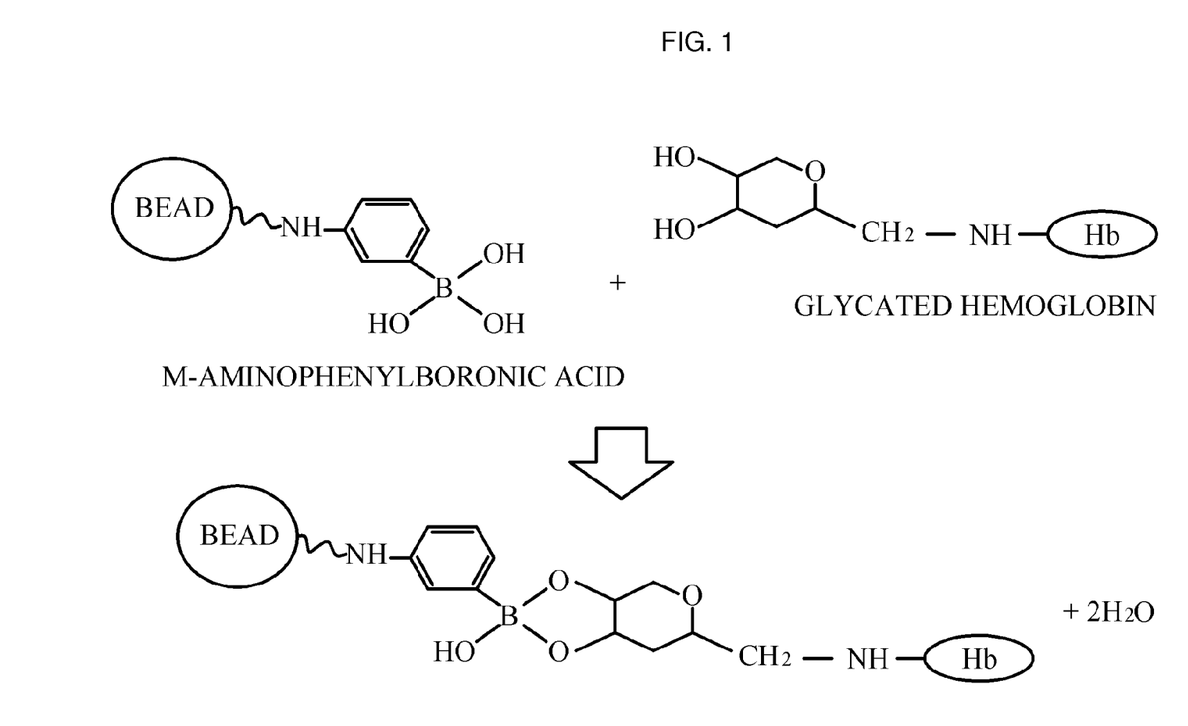
FIG. 1 shows a chemical structure in which glycated hemoglobin reacts with a bead conjugate that uses boronic acid as a glycated hemoglobin binding material.

FIG. 1 illustrates a chemical structure in which glycated hemoglobin reacts with a bead conjugate that uses boronic acid as a glycated hemoglobin binding material. As illustrated in FIG. 1, an OH functional group of the boronic acid and cis-diol of sugar bound to a terminal of the glycated hemoglobin react with each other, forming a pentagonal ring structure. The boronic acid is specifically bound to only the glycated hemoglobin of the total hemoglobin using this characteristic.

Thus, when a marker is attached to the glycated hemoglobin binding material, only the glycated hemoglobin can be selectively marked. In the related art, a dye or a magnetic material is attached to the glycated hemoglobin binding material, thereby distinguishing the glycated hemoglobin. In contrast, in the present invention, a bead having a predetermined size is used to isolate the glycated hemoglobin.

The bead that may be used in the present invention may be at least one of a polymer polysaccharide support such as agarose, cellulose, or sepharose, a latex bead such as polystyrene, polymethylmethacrylate, or polyvinyltoluene, and a glass bead, preferably a sepharose bead.

The bead used in the present invention does not act as a dye, but functions to allow the glycated hemoglobin to be isolated from normal hemoglobin by its volume in the following step. Here, a diameter of the bead is preferably selected in consideration of a precipitation time of the glycated hemoglobin binding material-bead bound with the glycated hemoglobin after reaction as well as reactivity with the glycated hemoglobin.

Meanwhile, the hemolysis step and the reaction step may be performed individually. Preferably, they may be implemented as a single step by putting the hemolysate and the bead conjugates into the blood sample at the same time.

In the hemolysis and reaction steps, it is preferable to agitate a cartridge used as a reaction container so as to accelerate a reaction of the blood sample with the hemolysate and the bead conjugates. This is intended to hemolyze the blood sample with the hemolysate to release the glycated hemoglobin and simultaneously guide a specific reaction of the glycated hemoglobin with the bead conjugates. Here, to allow the hemolyzed blood sample to sufficiently react with the bead conjugates, a predetermined time, for instance 3 minutes, may be required.

Figure 2A:
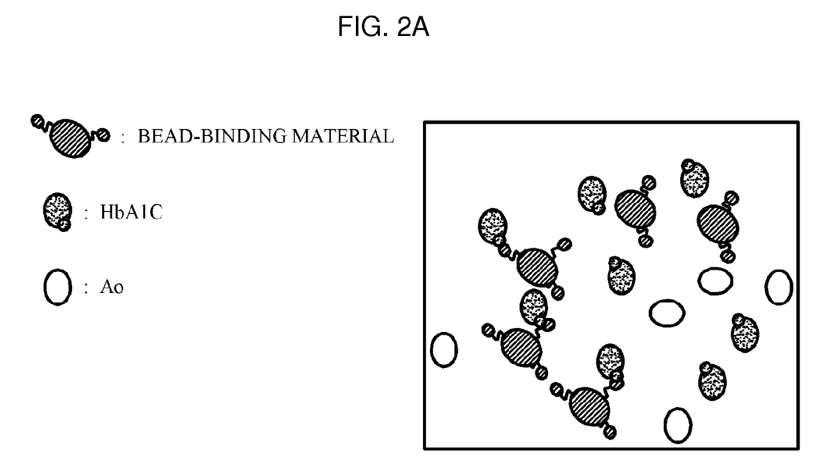
FIG. 2 schematically shows a reaction step (FIG. 2(a)) of the present invention, a state in which normal hemoglobin and glycated hemoglobin conjugated with bead conjugates coexist in a sample after the reaction step (FIG. 2(b)), and a state in which normal hemoglobin is removed (FIG. 2(c)).
Figure 2B:
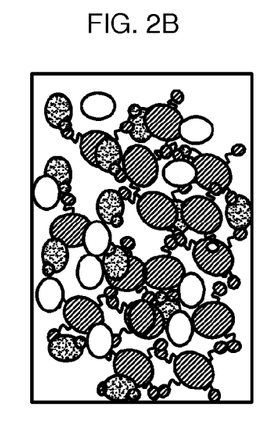
Figure 2C:
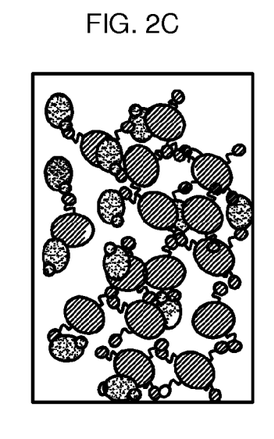

As shown in FIG. 2, after the hemolysis and reaction steps, normal hemoglobin and the glycated hemoglobin to which the bead conjugates are attached coexist in the blood sample. At this time, an amount of total hemoglobin in blood is measured. That is, FIG. 2(a) shows a process in which the bead conjugates are attached to the glycated hemoglobin, and FIG. 2(b) shows the state of total hemoglobin in which both marked glycated hemoglobin and normal hemoglobin are contained. Further, FIG. 2(c) shows the state where only glycated hemoglobin is left after normal hemoglobin is removed from a blood sample.

Figure 3:
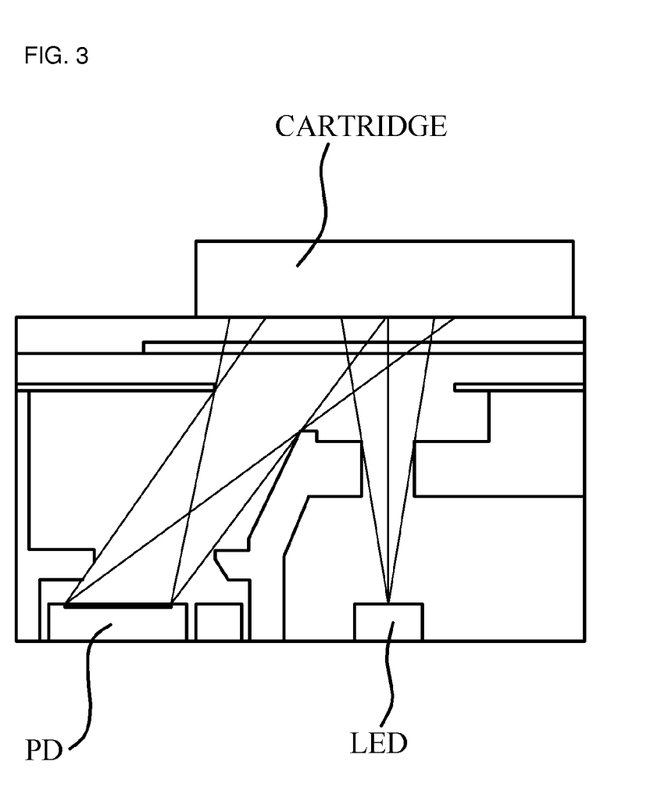
FIG. 3 shows an illustrative process of measuring a concentration of hemoglobin.

That is, in the state where the glycated hemoglobin to which the bead conjugates are attached is present along with the normal hemoglobin, the first measuring step of measuring the concentration of total hemoglobin in the blood is performed. An amount of glycated hemoglobin can be measured on the basis of measurement using a light reflective characteristic. For example, when the amount of glycated hemoglobin of the blood sample is to be measured, a characteristic of the hemoglobin that specifically absorbs an optical signal having a specific frequency is used. Here, a glycated hemoglobin measuring instrument preferably measures the amount of glycated hemoglobin using a light emitting device such as a light emitting diode and a light receiving device such as a photodiode. FIG. 3 shows an illustrative measuring process. As shown in FIG. 3, to measure the concentration of hemoglobin, the reaction is preferably performed in a cartridge including a transparent measuring window.

In other words, the light emitting device emits an optical signal having a specific wavelength. For example, when the amount of glycated hemoglobin is to be measured, the light emitting device may emit an optical signal having a wavelength of about 340 nm which the hemoglobin of the blood sample specifically absorbs. Here, the light-receiving device receives the optical signal that has been emitted from the light emitting device and has passed through the cartridge. That is, a light emitting control signal is output to the light-emitting device, and the optical signal input from the light-receiving device is converted into an electrical signal using an analog-to-digital (A/D) converter. Thereby, the amount of hemoglobin contained in the cartridge can be measured.

In the related art, to prevent the beads attached to the glycated hemoglobin from influencing a value of measurement of the amount of glycated hemoglobin, an amount of total hemoglobin in the blood is detected prior to the attachment of the beads. To measure the amount of glycated hemoglobin, a step of dissociating the glycated hemoglobin attached to the bead conjugates must be performed. In contrast, the inventors of the present invention have found that no influence is exerted on a value of measurement of the amount of total hemoglobin even when the bead conjugates are attached to the glycated hemoglobin as can be seen from Embodiment 1, thereby making it possible to omit an unnecessary step.

Next, to obtain the concentration of glycated hemoglobin, the isolation step of isolating the normal hemoglobin from the glycated hemoglobin bound with the bead conjugates must be performed. Preferably, the isolation step may be performed by absorbing only the normal hemoglobin using an absorption pad.

Figure 4:
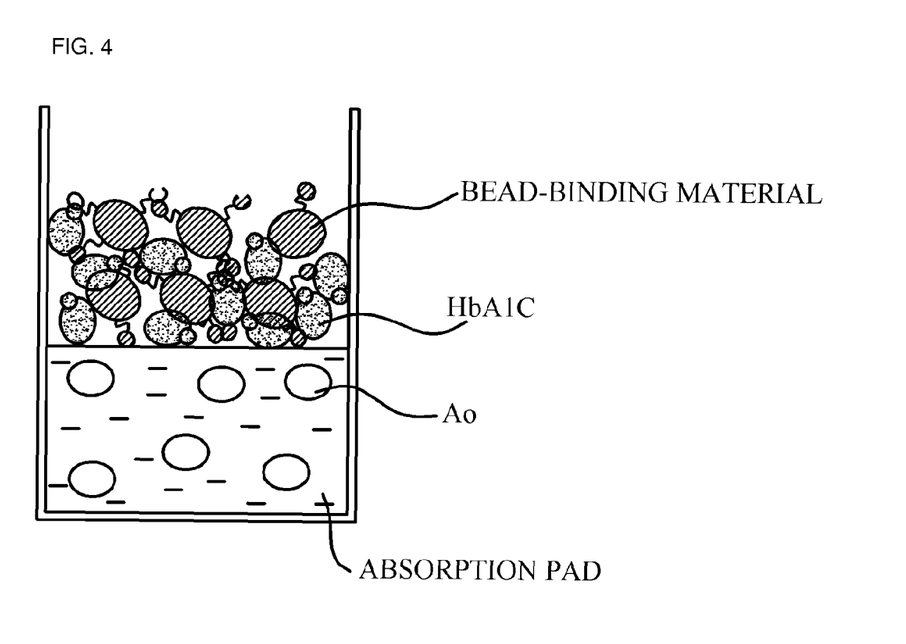
FIG. 4 schematically shows a state in which normal hemoglobin is absorbed into an absorption pad, and glycated hemoglobin conjugated with bead conjugates is isolated separately.

In the present invention, a porous pad may be used as the absorption pad. A size of each pore formed in the porous pad must be greater than a size of the hemoglobin and be smaller than a size of the bead. In greater detail, a porous pad formed of one selected from polyester, polyurethane, etc. may be used. As a result, as shown in FIG. 4, the normal hemoglobin is absorbed by the absorption pad, and the glycated hemoglobin conjugated with the bead conjugates is isolated separately. As a result, only the glycated hemoglobin conjugated with the bead conjugates is isolated and left on the measurement window.

The absorption pad absorbs a mixture of the blood sample after the measurement is completed, thereby blocking movement of the blood sample mixture. For example, as shown in FIG. 4, the absorption pad is preferably located under a measurement zone. The isolation step may be based on, but is not limited to, the absorption pad.

The isolation step is preferably performed by supplying a washing solution for higher reliability and shorter time of isolation. In the present invention, the washing solution may be selected from a group consisting of TRIS, HEPES, TES, and PIPES. As the washing solution washes the blood sample mixture, the ordinary hemoglobin Ao non-specifically present in the blood sample is removed.

In other words, most of the hemoglobin (Hb) in the red blood cells of the blood sample is non-glycated ordinary hemoglobin Ao. Here, only a range of 4 to 14% of the ordinary hemoglobin reacts with glucose, and is present as the glycated hemoglobin Hb $A_{1c}$. Thus, to measure the glycated hemoglobin in the blood, the ordinary hemoglobin must be removed. To this end, the washing solution capable of washing the ordinary hemoglobin is preferably used to more easily isolate the glycated hemoglobin so as to measure the glycated hemoglobin.

This results in leaving only the glycated hemoglobin on a measured bed. At this time, the second measuring step of measuring the concentration of isolated glycated hemoglobin is performed. The second measuring step may be performed in the same manner as the first measuring step. That is, it is preferable that the second measuring step also be performed on the basis of light reflection measurement using an optical sensor.

Then, the amount of total hemoglobin is divided by the amount of glycated hemoglobin, so that a relative amount of glycated hemoglobin in the blood sample is measured. Here, the percentage of the glycated hemoglobin is calculated by the following equation.

Percentage(%)of glycated hemoglobin=glycated hemoglobin/total hemoglobin×100

As described above, the reaction is preferably performed in the cartridge having the measurement zone so as to easily measure the concentration of the hemoglobin. The "measurement zone" refers to a zone where the amounts of hemoglobin and glycated hemoglobin of the blood sample in the cartridge are measured, and may indicate a zone located on the absorption pad in FIG. 4. Here, the amount of hemoglobin may be measured within the measurement zone on the basis of the light reflective characteristic measurement. For example, the characteristic of the hemoglobin of specifically absorbing the optical signal having a specific frequency may be used. Since intensity or contrast of light can be compared by the characteristic of the hemoglobin, the concentration of hemoglobin can be measured. Furthermore, the measurement zone may further include an optical window from which the light received through an external optical sensor is reflected to measure the light reflection characteristic.

The present invention will be described with reference to the following embodiments, which are intended to be illustrative. Thus, the present invention is not limited to these embodiments.

MODE FOR INVENTION

Embodiment 1

Preparation of Bead Conjugates in which Beads are Conjugated with Glycated Hemoglobin Binding Materials (1) Washing Step CM sepharose beads were washed three times with distilled water so as to have the total volume of 1 L, and then twice with 100 mM of 2-(N-morpholino)ethanesulfonic acid (MES) with a pH of 4.7. Here, the washing method was adapted to add a buffer, precipitate the buffer, and discard an upper stratum of the buffer. In the washing step, the beads were subjected to removal of a remaining ethanol component, and conversion into high-yield optimal synthetic pH of 1-ethyl-3-[3-dimethylaminopropyl]carbodiimide hydrochloride (EDC or EDAC).

(2) Conjugating Step

EDC or EDAC is a zero-length crosslinking agent used to couple carboxyl groups to primary amines. When this crosslinking agent was used, the carboxyl groups coupled to CM sepharose and the amine groups of 3-aminophenylboronic acid (3-APBA) could be conjugated to synthesize APBA beads.

46 g of EDC and 4.65 g of APBA were dissolved in 100 mM MES (pH 4.7), sequentially added to a bead solution, and reacted at 4° C. for two hours. Since APBA is sensitive to light, the reaction had to be performed in a dark place. Since EDC absorbs moisture, care had to be taken to store it in a sealed state after it was weighed.

A step of adding and synthesizing the EDC as the crosslinker and the boronic acid as the synthetic material was performed at a low temperature in order to enhance efficiency of, for instance, producing a synthetic by-product.

(3) Quenching and Blocking Steps 1M sodium acetate solution (in dry weight (DW)), 100 mM acetic acid solution (in DW), 50 mM NaOH solution (in DW), and 1 M NaCl solution (in DW) were each added at 500 mL, and were reacted at room temperature for one hour. At this time, since the reactant is sensitive to light, the reaction was performed in a dark place. The EDC left after the synthesis was completed was quenched with sodium acetate, and was washed and blocked with acetic acid, NaOH, and NaCl.

(4) Washing Step

Finally, the bead conjugates were washed three times with distilled water, and then twice with 20 mM HEPES (pH 8.1), and were adjusted to a final pH of 7.4.

The chemical structure in which the bead conjugate using the aminophenyl-boronic acid (APBA) as the glycated hemoglobin binding material reacted with the glycated hemoglobin is illustrated in FIG. 1. As illustrated in FIG. 1, the OH functional group of the boronic acid and the cis-diol of sugar bound to the terminal of the glycated hemoglobin react with each other, forming the pentagonal ring structure. The boronic acid is specifically bound to only the glycated hemoglobin of the total hemoglobin using this characteristic.

Embodiment 2

Effect of Beads on Value of Measurement of Glycated Hemoglobin

The following experiment was conducted to check whether reflective light was uniformly measured according to an amount of total hemoglobin regardless of refraction according to the size of beads or an amount of glycated hemoglobin specifically conjugated to the beads.

The following samples were prepared by centrifuging ten samples including blood of diabetic and normal persons, and adjusting a ratio of blood plasma and precipitated red blood cells.

An amount of total hemoglobin was measured using Hb 201 (HemoCue, Sweden).

Two samples having a range of 0 to 5 g/dl
Three samples having a range of 5 to 10 g/dl
Two samples having a range of 11 to 15 g/dl
Three samples having a range of 15 to 20 g/dl CLOVER A1C (INFOPIA Co. Ltd.) was converted into a factory mode. In the factory mode, the intensity of reflective light was displayed on a liquid crystal display (LCD) as raw data. A CLOVER A1C CARTRIDGE (INFOPIA Co. Ltd.) was inserted into the CLOVER A1C, and then a mixture of a hemolysate and bead conjugates was injected into a reaction zone at 700 ul. Each sample was well agitated, and then injected into the hemolysate at 4 ul. The machine was operated. After 5 minutes has lapsed, the data displayed on an LCD screen of the CLOVER A1C CARTRIDGE was read.

The results were as in Table 1 below.

TABLE 1

(correlation between the amount of hemoglobin and the value of k/s)

| Sample No. | Glycated hemoglobin (%) | Total hemoglobin (g/dl) | k/s |
|---|---|---|---|
| 1 | 5.1 | 2.8 | 0.152 |
| 2 | 7.6 | 6.0 | 0.339 |
| 3 | 5.2 | 11.1 | 0.720 |
| 4 | 5.3 | 7.4 | 0.490 |
| 5 | 8.6 | 4.5 | 0.255 |
| 6 | 9.6 | 20.0 | 1.219 |
| 7 | 6.7 | 12.9 | 0.837 |
| 8 | 5.4 | 18.5 | 1.157 |
| 9 | 10.1 | 9.3 | 0.563 |
| 10 | 4.9 | 17.0 | 1.043 |

Figure 5:
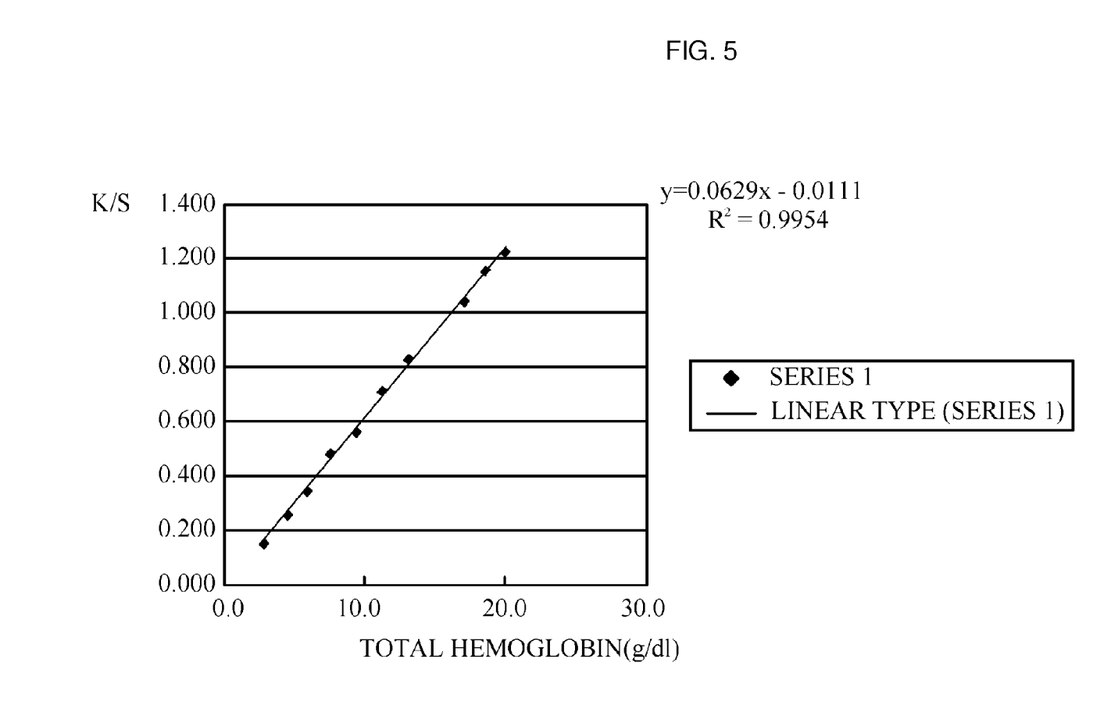
FIG. 5 is a graph showing that the presence of beads has no influence on a value of measurement of a concentration of hemoglobin.

The results are depicted in the graph of FIG. 5. In the graph, an x axis indicates the amount of total hemoglobin, and a y axis indicates the value of k/s. The value of k/s refers to the intensity of reflective light.

It can be seen from FIG. 5 that there is a correlation between the x and y axes. As the amount of total hemoglobin varies, the reflective light of the beads uniformly varies in proportion to such variation.

While the invention has been shown and described with reference to certain exemplary embodiments thereof, it will be understood by those skilled in the art that various changes in form and details may be made therein without departing from the spirit and scope of the invention as defined by the appended claims. Accordingly, the disclosed embodiments should be taken as exemplary and not limiting. The scope of the invention is defined in the claims rather than the detailed description, and all differences within the equivalent range should be interpreted as being included in the invention.

The invention claimed is:

1. A method for measuring glycated hemoglobin, the method comprising:
    a hemolysis step of hemolyzing a blood sample with a hemolysate;
    a reaction step of reacting the hemolyzed blood sample with bead conjugates in which beads are conjugated with glycated hemoglobin binding materials;
    a first measuring step of measuring the amount of total hemoglobin in the reacted blood sample;
    an isolation step of isolating normal hemoglobin from glycated hemoglobin bound to the bead conjugates, wherein the glycated hemoglobin bound to the bead conjugates is isolated from normal hemoglobin in the reacted blood sample;
    a second measuring step of measuring the amount of glycated hemoglobin isolated from the normal hemoglobin; and a calculation step of determining the percentage of the glycated hemoglobin in the blood sample on the basis of the measured amounts of total hemoglobin and glycated hemoglobin, wherein the isolation step is performed by absorbing the normal hemoglobin using an absorption pad which is a porous pad having pores, each of which has a size greater than the size of the normal hemoglobin and smaller than the size of the bead.

2. The method according to claim 1, wherein the hemolysis and reaction steps are performed as a single step by putting the hemolysate and the bead conjugates into the blood sample at the same time.

3. The method according to claim 1, wherein the hemolysate is selected from the group consisting of Tris(hydroxymethyl)aminomethane hydrochloride (TRIS), N-2-ydroxyethylpiperazine-N'-2-ethanesulfonic acid (HEPES), N-[Tris(hydroxymethyl)methyl]-2-aminoethanesulfonic acid (TES), and 1,4-Piperazinediethanesulfonic acid (PIPES).

4. The method according to claim 1, wherein the bead is at least one of an agarose bead, a cellulose bead, a sepharose bead, a polystyrene bead, a polymethylmethacrylate bead, a polyvinyltoluene bead, and a glass bead.

5. The method according to claim 1, wherein the glycated hemoglobin binding material is at least one of boronic acid, concanavalin A, and an antibody.

6. The method according to claim 1, wherein the first and second measuring steps are performed on the basis of light reflection measurement using an optical sensor.

7. The method according to claim 1, wherein the isolation step is performed by supplying a washing solution.

8. The method according to claim 7, wherein the washing solution is selected from the group consisting of Tris(hydroxymethyl)aminomethane hydrochloride (TRIS), N-2-ydroxyethylpiperazine-N'-2-ethanesulfonic acid (HEPES), N-[Tris(hydroxymethyl)methyl]-2-aminoethanesulfonic acid (TES), and 1,4-Piperazinediethanesulfonic acid (PIPES).

* * * * *